United States Patent
Olshavsky et al.

(10) Patent No.: US 6,732,744 B2
(45) Date of Patent: May 11, 2004

(54) METHOD FOR THE ULTRASONIC TREATMENT OF HAIR AND OTHER KERATINOUS FIBERS

(75) Inventors: Michael Andrew Olshavsky, Mason, OH (US); Ke Ming Quan, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 145 days.

(21) Appl. No.: 10/010,456

(22) Filed: Dec. 7, 2001

(65) Prior Publication Data

US 2003/0106564 A1 Jun. 12, 2003

(51) Int. Cl.[7] ............................................... A45D 24/00
(52) U.S. Cl. .................................................... 132/200
(58) Field of Search ............................. 132/200, 119.1, 132/148, 118, 271; 607/79, 103, 109, 110, 2

(56) References Cited

U.S. PATENT DOCUMENTS

| | | | |
|---|---|---|---|
| 3,158,635 A | 11/1964 | Kezerian et al. | |
| 3,202,579 A | 8/1965 | Berth et al. | |
| 3,211,159 A | 10/1965 | Goble | |
| 3,254,424 A | 6/1966 | Goble | |
| 3,281,948 A * | 11/1966 | Goble | 132/226 |
| 3,526,234 A | 9/1970 | Chrablow | |
| 3,542,918 A | 11/1970 | Berth et al. | |
| 4,023,579 A * | 5/1977 | Suroff | 132/226 |
| 4,085,893 A | 4/1978 | Durley, III | |
| 4,138,478 A | 2/1979 | Reese et al. | |
| 5,100,436 A | 3/1992 | Wenke | |
| 5,297,512 A * | 3/1994 | Sharp | 119/86 |
| 5,376,146 A | 12/1994 | Casperson et al. | |
| 5,635,167 A | 6/1997 | Said et al. | |
| 5,875,789 A * | 3/1999 | Shigihara | 132/210 |
| 6,145,513 A | 11/2000 | Chu et al. | |
| 6,159,916 A * | 12/2000 | Robbins et al. | 510/238 |
| 6,196,236 B1 * | 3/2001 | Imai et al. | 132/226 |

FOREIGN PATENT DOCUMENTS

| | | |
|---|---|---|
| DE | 100 56 062 A | 6/2002 |
| JP | 03-182203 | 8/1991 |
| JP | 97262120 A | 10/1997 |
| JP | 97308516 | 12/1997 |
| JP | 2001 120335 A | 8/2001 |

* cited by examiner

Primary Examiner—Cary E. O'Connor
Assistant Examiner—Robyn Kieu Doan
(74) Attorney, Agent, or Firm—Peter D. Meyer

(57) ABSTRACT

The invention is the use of a chelating agent with an ultrasonic device for the treatment of hair and other fibers. The treatment device includes an ultrasound generator, a comb device responsive to the generated ultrasonic waves, a reflector for reflecting the incident ultrasonic waves disposed on the distal end of the comb device, and a chelating agent preferably disposed within the treatment device. The treatment device efficaciously dispenses the chelating agent and ultrasonically treats the fiber.

20 Claims, 4 Drawing Sheets

METHOD FOR THE ULTRASONIC TREATMENT OF HAIR AND OTHER KERATINOUS FIBERS

FIELD OF THE INVENTION

The invention is in the field of the use of ultrasonic devices for the treatment of keratinous fibers with a chelant.

BACKGROUND OF THE INVENTION

Bleaching and dyeing keratinous fibers, such as hair, has become increasingly popular. This technology enables people to change the natural color of a fiber to a potentially more fashionable color, or to conceal imperfections present within a natural fiber. However, these methods are slow, laborious, ineffective, not topically efficacious, and the chemical agents used can damage the treated fiber.

In these processes, the desired color is produced by chemically treating the naturally produced fiber pigment, melanin. Melanin is formed in a hair bulb at the root of the hair and deposited into the central part of the hair shaft, as the hair grows. The hair shaft, which has two major regions (the cuticle region (exterior) and a cortex region (interior)), comprises dead cells that have differentiated into a mixture of different forms of the hair protein, keratin. Keratin within the cuticle region, contains high concentrations of the amino acid cystine. Each cystine molecule comprises two cystine amino acids cross-linked by a disulfide bond that provides the cuticle with most of its hydrophobic properties, physical durability, and stability to swelling. The cuticle is a protective layer for the hair, preserving the integrity of the cortex. The cortex provides rigidity and most of the mechanical properties to the hair fiber.

A typical hair lightening process achieves a lightening effect by oxidation of the melanin pigments using bleaches. Bleaches typically comprise an oxidizing agent in an alkaline solution. Typical oxidizing agents are hydrogen peroxide, potassium, sodium, or ammonium salts of perborate or percarbonate, persulfate, and percarbamate.

The traditional permanent coloring process utilizes permanent, or oxidative, dyes consisting of small molecules capable of diffusion into the hair fiber. Typically, these molecules belong to three classes of aromatic compounds: diamines, aminophenols, and phenols. The small size of these molecules facilitates diffusion into the hair shaft where they are activated by an oxidative material to form a larger colored complex within the hair shaft.

However, these oxidative treatments have several drawbacks. First, effective bleaching and dyeing processes damage hair due to the aggressive and chemically indiscriminate nature of the oxidizing agents. The oxidizing agent penetrates and damages the cuticle en-route to the cortex, where melanin oxidation occurs. This damage is particularly exacerbated by repeated use of high pH oxidation treatment compositions. Repeated treatments destroy the keratin disulfide bonds resulting in cuticle degradation and subsequent cortex damage resulting in decreased fiber strength and weak, brittle hair. Thus, the capability of the composition to produce desired cosmetic changes such as light shade, color evenness, color fading, general hair feel, shine, and/or luster is decreased.

Chelants can be applied to a keratinous fiber to remove, mask, or inactivate bound minerals. Removing these minerals can lessen visible fiber damage. The effectiveness of a chelant is primarily a function of the rate of penetration of the chelant into the fiber. A typical chelant-based treatment comprises a step where a hair fiber is contacted with a blend of chelating agents at a concentration of 4 to 25 percent w/w and a pH ranging between 4 and 10.

Additionally, devices incorporating ultrasonic mechanical vibrations are well known in the art. Ultrasonic mechanical vibrations are generally produced by Piezoelectric devices. Piezoelectric devices convert electrical impulses into mechanical vibrations by developing a mechanical motion by deforming certain crystals under pressure. Resonant crystals and ceramics are used to generate such mechanical waves in solids and liquids. For high frequency, ultra-sonic vibrations to be generated, crystals operate in their thickness mode (the crystal becomes alternatingly thicker and thinner as it vibrates.)

While the materials described are suitable for bleaching or dying a hair fiber, the nature of the process by which a fiber is dyed can be process sensitive. For example, the maximum speed at which such treatment occurs can be limited by the effectiveness of the chelant molecule, the treatment time, the rigor of the treatment, and/or the concentration of chelant in the compound. Accordingly, it would be desirable to provide an improved process suitable to treat fibers with a chelant. It is desirable to reduce the deleterious effects described above. It would be an improvement in the art to provide a novel process to treat a keratinous fiber, such as hair, using less chemical agent, and provide a faster, less labor intensive, and more topically efficacious treatment experience.

SUMMARY OF THE INVENTION

In a non-limiting exemplary embodiment of the present invention, the process for the oxidative treatment of keratinous fibers comprises placing a chelant proximate to a keratinous fiber and placing an ultrasonic treatment device proximate to the keratinous fiber. The ultrasonic treatment device is energized to produce a topically efficacious energy. The topically efficacious energy is applied from the ultrasonic treatment device to the keratinous fibers so that the topically efficacious energy efficaciously deposits the chelant onto the keratinous fiber.

In yet another alternative embodiment of the present invention, the process for the oxidative treatment of keratinous fibers comprises providing an ultrasonic treatment device comprising a comb device, a first material reservoir for supplying a first material, a second material reservoir for supplying a second material so that the first material reservoir and the second material reservoir are in liquid communication with the comb device. At least one of the first material or the second material is dispensed from the ultrasonic treatment device onto the keratinous fibers. The ultrasonic treatment device is energized to produce a topically efficacious energy. The topically efficacious energy is applied from the ultrasonic treatment device to the keratinous fibers.

In yet another embodiment of the present invention, a kit comprising at least one chelant and at least one active agent combined in a container is provided for the oxidative treatment of keratinous fibers.

DETAILED DESCRIPTION OF THE INVENTION

Figure 1:
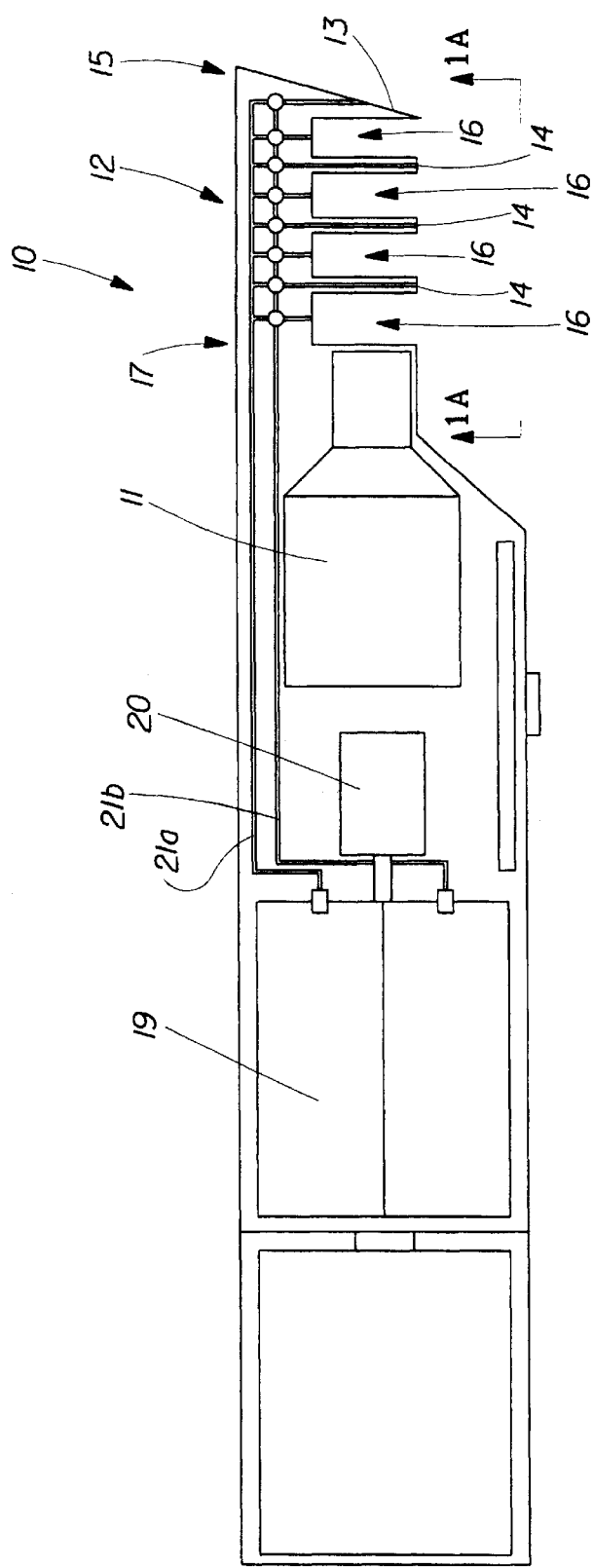
FIG. 1 is an exemplary embodiment of an ultrasonic fiber treatment device suitable for use and in accordance with the present invention.
Figure 1A:
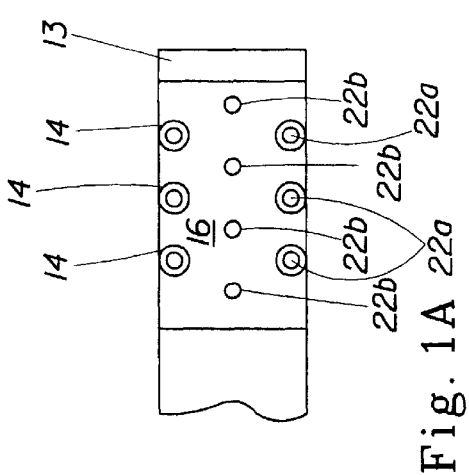
FIG. 1A is a cross-sectional view of the ultrasonic fiber treatment device taken along the line 1A—1A.

The present invention is related to the use of an ultrasonic device for the application of a chelant to fibers such as keratinous fibers, typically hair. The purpose for utilization of ultrasonic energy with a chelant process is not limited to, but includes, providing a more efficient manner in which to treat a fiber with a chelant. Increased efficiency can reduce the required amount and concentration of chelant necessary. Additionally, treatment time can be reduced, thereby providing a time saving way to provide long-term fiber care and increased damage protection against oxidation during bleaching, at a reduced cost. It has also been surprisingly found that the use of ultrasound in the chelant application process results in an enhanced diffusion of relatively large chelant molecules into a fiber, by temporarily increasing the fiber pore size. This is particularly true of Cu-selective chelants having molecular weights in the range of 300–400 versus the traditional hydrogen peroxide (mol. wt.=34) oxidative bleaching agent.

Chelant

As used herein, the term "oxidative treatment of fiber" is intended to encompass all treatments of fibers comprising at least one step of contacting a fiber with at least one oxidizing composition. Non-limiting examples of oxidative treatments include hair bleaching, hair highlighting, hair dyeing, hair perming, and hair straightening.

The term "oxidizing composition" means a composition comprising at least one oxidizing agent such as, but not limited to, hydrogen peroxide, sodium, potassium, ammonium or other salts of perborate, percarbonate, persulfate, and percarbamate.

The term "chelant" defines a molecule containing two or more electron donor atoms that can form a coordination bond to a single ion, such as a metal. After the formation of the first such coordinate bond, each successive donor atom that binds creates a ring containing the metal ion. The cyclic structure that is formed is called a chelate. Chelants are widely used as stabilizing agents in compositions containing hydrogen peroxide.

Members of a class of diamine or monoamine monoamide-N,N'-dipolyacids, N,N'-bis(2-hydroxybenzyl) ethylenediamine-N,N'-diacetic acids, precursors thereof, salts thereof, and combinations thereof, show excellent oxidative damage inhibiting properties over other known chelants, especially EDTA. In particular, these chelants are especially efficient at a pH greater than 8. Additionally, amine-based chelants improve the efficiency of an oxidizing agent and provide a better feel to the fiber after treatment. The chelant may have a concentration from about 0.5 to about 40 percent by weight, more preferably about 0.5 to about 10 percent by weight, and most preferably from about 2 to about 5 percent by weight.

As a non-limiting example, diamine-N,N'-dipolyacids suitable for use can be synthesized by the reaction of a diamine with an anhydride or an unsaturated polyacid. Diamine starting materials for the preparation of diamine-N,N'-dipolyacids include diamines having the general formula:

$R_1R_2N-(CH_2)_n-NR_3R_4$, where $R_1$, $R_2$, $R_3$, and $R_4$ are typically hydrogen or $C_1$ to $C_4$ alkyl or alenyl groups, n is an integer from 1 to 8, and the $CH_2$ units are optionally substituted with hydroxyl or amino groups. Preferred diamines include, but are not limited to, ethylene diamine, 1,3-propylene diamine, and 2-hydroxy-1,3-propylenediamine. Further, any anhydride or unsaturated polyacid capable of reacting with a diamine to form a diamine-N,N'-dipolyacid may also be used. An exemplary, non-limiting, anhydride is maleic anhydride. An exemplary, non-limiting, unsaturated polyacid is maleic acid. Preferred diamine dipolyacids, derived from diacids and suitable for use herein include, but are not limited to, ethylenediamine-N,N'-disuccinic acid (EDDS), ethylenediamine-N,N'-diglutaric acid (EDDG), 2-hydroxypropylenediamine-N,N'-disuccinic acid (HPDDS), precursors thereof, salts thereof, and combinations thereof. An exemplary, but non-limiting preferred monoamine monoamide-N,N'-dipolyacid is glycinamide-N,N'-disuccinic acid (GADS), precursors thereof, salts thereof, and combinations thereof. An exemplary, but non-limiting preferred N,N'-bis(2-hydroxybenzyl)ethylenediamine-N,N'-diacetic acid is ethylenediamine-N-N'-bis(ortho-hydroxyphenyl) acetic acid (EDDHA), precursors thereof, salts thereof, and combinations thereof. An exemplary method for forming EDDS is found in U.S. Pat. No. 3,158,635, issued to Kezerian, and herein incorporated by reference.

Active Agent

The chelant is typically used in combination with at least one active agent, such as an oxidizing composition. The active agent preferably comprises a water-soluble peroxygen oxidizing agent. "Water soluble" means a compound that can be substantially solubilized in water. Such water-soluble peroxygen oxidizing materials are valuable for the initial solubilization and decolorization of the melanin within the fiber substrate.

Peroxygen bleaching compounds useful are generally peroxygen materials capable of yielding hydrogen peroxide in an aqueous solution. Non-limiting examples of such water-soluble peroxygen oxidizing compounds include hydrogen peroxide, inorganic alkali metal peroxides such as sodium periodate and sodium peroxide, organic alkali peroxides such as urea peroxide, melamine peroxide, and inorganic perhydrate salt bleaching compounds such as the alkali metal salts of perborates, percarbonates, perphosphates, persilicates, persulphates, and the like which may be incorporated as monohydrates or tetrahydrates.

The active agent present in the compositions of the present invention may be applied from about 0.5 to about 40 percent by weight of the composition. When the oxidizing composition and the composition comprising the oxidative damage inhibitor are provided separately and used in combination, the level is expressed in weight percent of the composition. Further, the weight percent of oxidizing agent to oxidative damage inhibiting chelant (e.g. EDDS) should be adjusted to be in the range from about 20:1 to about 1:20, preferably from about 9:1 to about 1:1, and most preferably 6:1.

Fiber Treatment Device

FIG. 1 depicts an embodiment of a fiber treatment device 10. Fiber treatment device 10 generally comprises an ultrasound generator 11 and comb device 12. Comb device 12 has a proximal end 17 and a distal end 15, and comprises a device for converging fibers into a region proximate to ultrasound generator 11. A reflector 13 is attached to the distal end 15 of comb device 12. Comb device 12 is preferably physically coupled to ultrasound generator 11. However, as would be known to one of skill in the art, it is possible to provide ultrasound generator 11 and comb device 12 as separate components without physical attachment. If physical coupling or attachment is desired, an insulator material can be provided between comb device 12 and the ultrasound generator 11. Alternatively, physical attachment can be accomplished by attaching comb device 12 to an insulative housing encasing ultrasound generator 11.

Preferably, comb device 12 is acoustically insulated from ultrasound generator 11. Acoustic insulation or acoustically insulated as used in the present invention means that comb device 12 is not acoustically resonant with ultrasound generator 11. This means that comb device 12 remains stationary while ultrasound generator 11 is active.

Physical coupling and acoustic insulation can be accomplished by the choice of construction and the method of physical attachment of comb device 12 to ultrasound generator 11. Because comb device 12 is preferably not acoustically coupled to ultrasound generator 11, the materials selected to manufacture comb device 12 should preferably be insulative in nature, such as plastic or wood. However comb device 12 can be manufactured from metal and provide no acoustic coupling, for example, by providing an acoustic insulator between ultrasound generator 11 and comb device 12. Additionally, polymeric materials can be impregnated with a metal, or metals, to provide an acoustically insulated comb device 12 that provides an efficacious, ultra-sonic, fiber treatment. A metal impregnated polymer can provide a more resilient structural device, yet still provide the physical acoustic insulative ability required.

Comb device 12 also comprises a reflector 13 designed to have a reflectance, R, expressed as:

$$R = \frac{Z_2 - Z_1}{Z_2 + Z_1}.$$

where, $Z_1$=the acoustic impedance of wet fiber, and, $Z_2$=the acoustic impedance of the reflector. $Z_1$ and $Z_2$ are defined by the equations:

$$Z_2 = \rho_2 c_2 \text{ and,}$$

$$Z_1 = \rho_1 c_1$$

where, $\rho_1$=the density of wet fiber, $\rho_2$=the density of the reflector, $c_1$=the acoustic velocity in wet fiber, and, $c_2$=the acoustic velocity in the reflector. Acoustic velocity is the speed at which a pressure wave propagates in the selected medium. Values for the acoustic velocity and density of exemplary fibers and other materials are tabulated below. However, the values of acoustic velocity and density for numerous other fibers and materials can be found in *The Handbook of Chemistry and Physics*, 78th edition, *Fundamental Physics of Ultrasound*, by V. A Shutilov, *Chemical and Physical Behavior of Human Hair*, 3d ed., by Clarence R. Robbins, and *IEEE Transactions on Sonics and Ultrasonics*, Vol. SU-32, No. 3 (1985), pages 381–394, all of which are herein incorporated by reference.

| Material | Density, $\rho$, (g/cm$^3$) | Velocity, c, (m/s) |
|---|---|---|
| Air | 1.161 × 10$^{-3}$ | 334 |
| Water | 0.998 | 1490 |
| Aluminum Alloy | 2.7 | 6260 |
| Human Hair Fiber | 1.3 | 1717 |
| Nylon Fiber | 1.12 | 2600 |

Reflector 13 is preferably attached to the distal end 15 of comb device 12 to form an open cavity 15 between reflector 13 and ultrasound generator 11. It is preferred that the materials selected to construct the reflector 13 provide an overall reflectance, R, so that $|R|>0$, and more preferably the materials selected to construct the reflector 13 provide an overall reflectance, R, so that $|R| \geq 0.5$.

Therefore, the inner surface, that is, the surface of reflector 13 closest to ultrasound generator 11, should be constructed of a material that effectively reflects acoustic waves generated by ultrasound generator 11. Exemplary and non-limiting reflective materials include metals and porous materials, such as wood. Most preferably, reflector 13 is constructed to have a thin metal sheet, film, or foil that has a region of air behind and positioned away from ultrasound generator 11 so that an acoustic vibration originating from ultrasound generator 11 will be significantly reflected in an opposite direction from the incident wave. This is generally known in the art as an air-backed reflector. Without desiring to be bound by theory, it is believed that such a reflector is effective because air generally has significant contrasting acoustic impedance relative to any liquid or solid material.

In a preferred embodiment, the distal end 15 of comb device 12 is also provided with a plurality of protuberances 14 to increase the coupling of fibers located between ultrasound generator 11 and reflector 13. Preferably, protuberances 14 are not affected by ultrasound generator 11 and form no part of the overall ultrasonic mathematical equation provided supra.

Special considerations should be given to the choice of the cavity 16 size incorporated into comb device 12, for instance, depth, width and length, so that within the cavity 16, the ultrasonic field is uniform to provide even fiber treatment. Outside the cavity 16, the ultrasonic field intensity decays rapidly and should minimally impact fibers outside the defined periphery of comb device 12. This decay makes an ultrasonic treatment safe for fibers and other unintended objects, especially hair dyeing, even in the hair root region where the skin on the scalp is in the vicinity of the operative fiber treatment device 10. Additionally, the optimum size of the cavity 16 depends on the applied ultrasonic frequency, f. For example, the optimum length, L, of the cavity 16 can be expressed by the equation:

$$L = kf$$

where k is a linear coefficient determined by the slope of the line comparing optimal comb length, L, to applied frequency, f. Preferably, exemplary and non-limiting values for k have been found to range from 0.009 cm/KHz to 0.020 cm/KHz. Most preferably the value for k is 0.013 cm/KHz.

Power for ultrasound generator 12 can be provided by either conventional commercial methods and converted to a necessary voltage by power supply 18. Alternatively, batteries contained within fiber treatment device 10 can provide power for ultrasound generator 12. Internal batteries could enable fiber treatment device 10 to be placed within a recharging receptacle while not in use. The fiber treatment device 10 may be heated, or another source of heat may be supplied if a fiber treatment regimen requires thermal energy to provide a more efficacious treatment.

As shown in FIG. 1, fiber treatment device 10 preferably includes a number of reservoirs 19, optionally cartridges. One advantage of a multiple reservoir dispensing system is that materials that would be incompatible for storage together may be stored in separate reservoirs and then dispensed together for use. Because the materials are mixed at the point of use as needed, there is better control over the amount of product mixed, resulting in minimal or no wasted product.

Any suitable reservoir 19 may be utilized in the present invention. It should be understood that the reservoir utilized may be fully or partially internal, or external, to the fiber treatment device 10, and may or may not be removable from the fiber treatment device 10. Additionally, the reservoir 19 utilized may be refillable or disposable. Non-limiting examples of suitable reservoirs 19 include positive displacement type reservoirs, such as a cartridge, and pump-evacuated type reservoirs, such as sachets, bladders, blisters, and combinations thereof. It is also believed that pre-loaded cartridge reservoirs could be used as single use disposable cartridges, multiple use disposable cartridges, or refillable cartridges, and that empty cartridges may be available for loading with suitable materials by the end user.

In the practice of the present invention, the reservoir 19 may be adapted for dispensing equal or unequal amounts of material. The dispensing system may be utilized for the delivery of precise, controlled, or efficacious amounts of treatment materials. It is also preferred that one or more of the reservoirs 19 of the present invention be loaded with a fiber treatment material in a sequential fashion. Sequential dispensing may also be accomplished by sequentially dispensing from different reservoirs 19 or combinations of reservoirs 19. Further, it should also be understood that a number of repeatable sequences could also be dispensed from either one cartridge or a combination of cartridges.

Reservoirs 19 are placed within the reservoir holder with one or more of the reservoirs 19 in liquid communication with the comb device 12. Dispensing actuator 20 is adapted to dispense material from reservoir 19 through dispensing passageways 21a, 21b to comb device 12. At least one dispensing apertures 22a, 22b is fluidly connected to dispensing passageways 20a, 20b and release material either from an aperture 22b disposed on comb device 12, from an aperture 22a located on protuberance 14, or both. Thus, incompatible chemistries, or chemistries that, after mixing, have a finite shelf life are mixed and/or dispensed at the point of application directly to the fibers. Further, the chemistries are further mixed at the point of application by the presence of the mechanical, ultrasonic vibrations produced by ultrasound generator 11.

Additional ultrasonic devices suitable for use are detailed in U.S. application Ser. No. 09/945,227 entitled "Ultrasonic Device For The Treatment of Hair and Other Fibers", filed on Aug. 31, 2001 in the name of Ke Ming Quan, et al., and herein incorporated by reference.

Method of Treatment

A method of use for a fiber treatment device commensurate with the scope of the present invention provides for the treatment of fibers, more particularly keratinous fibers, and even more particularly, hair. It is preferred that a user pre-wets the fibers to be ultrasonically treated. Non-limiting examples for pre-wetting hair include rinsing with water and/or cleaning the hair fibers with a cleaner, such as shampoo, or a cleaner/conditioner, such as PertPlus™, manufactured by The Procter & Gamble Company. The chelant, and/or active compound, which can be supplied singly or in containerized kit form, is applied to the fibers in a topically efficacious amount to produce the results desired for the fiber being treated. Preferably, the chelant, and/or active compound, is dispensed directly from the fiber treatment device when the fiber treatment device is equipped with reservoirs containing the chelant, and/or active compound. However, if the fiber treatment device is not so equipped, the chelant, and/or active compound, can be manually applied to the fibers through conventional methodologies.

The operationally energized fiber treatment device is placed in contact with the treated fibers preferably using a steady and continuous motion from the root end of the fiber to the tip end of the fiber. Preferably, this motion is repeated until all desired fibers are efficaciously treated. It has been surprisingly found that approximately five minutes of treating fibers with a topically efficacious amount of an active compound using the ultrasonic fiber treatment device of the present invention is comparable to thirty minutes of treatment using prior art methods. Thus, the total time required to provide an efficacious treatment of a full head of hair can be reduced from current 30–40 minute procedures to approximately 5–10 minutes total treatment time with the present invention. Of course, the total time required to provide such a topically efficacious treatment will depend upon the length and thickness of the fibers being treated and the desired resultant color intensity. However, it has been found that when coloring hair with a visible root line or when coloring patched gray hair, it may be preferable to apply the use of the ultrasonic fiber treatment device for longer time periods than would normally be required for hair fibers not exhibiting these characteristics. Additional rinses and applications of chelant are possible to produce the desired result.

It is also envisaged that the exemplary procedure described supra can also be used for the topically efficacious treatment of pet hair fibers. Additionally, it is intended that fabric and other keratinous fibers can be treated using the ultrasonic fiber treatment device and a chelant as discussed above.

EXAMPLES

Damage to a hair fiber may be confined to the cuticle or to the entire fiber during chemical oxidation cosmetic treatments, such as bleaching or coloring. However, cuticle layers are generally damaged before any damage can occur to the cortex of the fiber. Therefore, damage tests that focus more on surface changes can be more sensitive than those that rely on whole fiber changes. Results of damage assessment of chemically oxidized hair using the surface sensitive technique of Scanning Electron Microscopy (SEM), can correlate strongly with data generated using other damage assessment methods.

Scanning Electron Microscopy

SEM has high resolution, a wide range of magnifications, and a high depth of focus and is suitable as a visualization technique for fiber quality analysis to examine the architecture of the cuticle. SEM can also quantify geometrical dimensions of fiber cross-sections (including determination of major and minor axis length), to characterize fiber fractures, and show alterations in fiber morphology due to cosmetic treatments including chemical oxidation and/or reduction.

Fourier Transform Infra-Red Analysis

Fourier Transform Infrared (FTIR) analysis is a suitable method for quantifying the amount of cysteic acid produced from the oxidation of cystine. It is believed that the oxidation of cystine is a suitable marker for monitoring the overall oxidation process of the keratinous fiber.

A Perkin-Elmer™ Spectrum 1 FTIR equipped with a diamond Attenuated Internal Reflection (ATR) was used to measure the cysteic acid concentration in hair fiber. The nominal FTIR conditions utilized a spectral resolution of 4 cm$^{-1}$, a data interval of 0.7 cm$^{-1}$, a mirror scan speed of 0.2 cm cm$^{-1}$, and a scan range of 4,000 cm$^{-1}$ to 600 cm$^{-1}$. Exemplary hair switches were platted (≈1 plait/cm) and were analyzed at four locations and results were recorded as a calculated average of the four readings. A background reading was made after every four measurements at an ATR cell pressure of 1 N/m. The resulting sample spectra were then converted to an absorbance measurement and then normalized to the characteristic protein $CH_2$ stretch band at 1450 cm$^{-1}$. The normalized absorbance reading was then twice derivatized using a 13 point averaging system, so that the values of the 1450 cm$^{-1}$ normalized second derivative of the absorbance at 1040 cm$^{-1}$ were taken as the as the relative concentration of cysteic acid. A cysteic acid concentration of less than about 150 is believed to provide the most efficacious topical result and still provide minimal oxidative damage.

Measurement of Lightening and Oxidative Damage

The level of bleaching and oxidative damage to subject hair switches was determined by comparative colorimetric measurements of the increase in lightening of the treated vigin hair substrate and the virgin hair substrate. The colorimetric measurements were made with a calorimeter manufactured by the Hunter Corporation. The comparative change in lightening was reported as ΔL in color space using L.a.b. coordinates.

Test Method

Hair bleaching using the bleaching process discussed supra was conducted over 5 bleaching cycles and the resulting cumulative ultrasonic oxidative damage was measured and compared to control samples. A bleach cycle included the application of a standard bleaching solution to a hair switch, followed by application of ultrasound directly to the hair switch for 10 minutes. The control samples used a bleach cycle applying a standard bleaching solution to a hair switch that was then wrapped in a plastic film and placed in an oven at 30° C. for 30 minutes.

The concentration of calcium and magnesium ions in the rinse treatment water was not modified from standard, municipally supplied potable water. The copper ion concentration of the treatment water was about 1 ppm, however, the exact concentration was gravimetrically determined. The rinsing water flow was maintained at 1.8 gallons/minute (6.8 liters/minute).

Three switches of virgin dark hair were used for each Example. "Virgin hair" means hair that has never been chemically treated. Such hair is available from Hugo Royer International Ltd, Berkshire, England. A switch typically weighed about 1.5 grams. Each switch was treated with a bleaching composition mixture having equal amounts, by weight, of hydrogen peroxide emulsion base and alkaline (high pH) emulsion base. The pH of the mixture was buffered to 10 by the alkaline emulsion base. The bleaching composition was applied to all virgin hair fiber switches at a rate of two grams per gram of hair fiber, and manually massaged in thoroughly. Select hair switches were treated for 10 minutes by contact with a Sonic & Materials® model VC 134 ultrasonic horn, at an output of 20 to 30 W at 25° C. and an acoustic frequency of 40 kHz.

All hair switches were then rinsed for 1 minute with water. Two replicate shampooings and 30 second milkings were conducted using 0.1 g of metal ion free Pantene® Clarifying shampoo, manufactured by The Procter & Gamble Company, having less than 0.1% by weight chelant, per gram of hair. Each switch was then rinsed for 30 seconds and then squeeze dried and fan dried. This procedure was repeated five times on each hair switch.

The hydrogen peroxide emulsion base contained:

a) 35% by weight of emulsion base premix comprising 10% stearyl alcohol and 5% cetereth25;
b) 25% stabilizing solution comprising 1% tetrasodium DTPA, 0.4% HEDP, 1% sodium hydroxide (32% purity) and water q.s.p;
c) 14% water; and,
d) 26% of 35% hydrogen peroxide.

The alkaline emulsion base contained:

a) 44.5% by weight of emulsion base premix comprising 10% stearyl alcohol and 5% cetereth25;
b) 0.2% by weight sodium sulphite;
c) 0.2% ascorbic acid;
d) 3% ammonium acetate;
e) 9.33% ammonia solution (30% purity);
f) chelant in the desired amount by weight; and,
g) q.s. water.

Example 1

Ultrasonic Bleach Formulation with EDDS

The bleaching composition described supra was formulated with a chelant comprising 2.0% wt/wt of the trisodium salt of EDDS and applied to triplicate selected hair switches over five replicate cycles using the method described supra.

Example 2

Ultrasonic Control Bleach Formulation

The bleaching composition described supra was formulated with an equivalent weight percent of deionized water in place of the chelant. This composition was applied over five cycles to another triplicate of virgin hair switches.

Example 3

Conventional Bleach Formulation with EDDS

The bleaching composition as described supra was formulated with a chelant comprising 2.0% wt/wt of the trisodium salt of EDDS. A triplicate of hair switches were treated and individually wrapped in a plastic film and heated at 30° C. for 30 minutes. Each switch was then removed from the oven and the film and rinsed for one minute in water. Each switch was then shampooed and rinsed as described supra, however, no ultrasonic treatment was used. This procedure was applied over five cycles to each hair switch.

Example 4

Conventional Control Bleach Formulation

A bleaching composition described supra was formulated with an equivalent weight percent of deionized water in place of the chelant. Each selected hair switch was treated with this composition and processed as described in Example 3.

All hair switches were then evaluated for the level of lightening from virgin hair using colorimetry. Oxidative damage was assessed using FTIR and SEM. The results of all measurements after five cycles are detailed in Table 1.

TABLE 1

Bleaching Level and Oxidative Damage vs. Formulation and Ultrasonic Application After Five Cycles

| Example | FIG. | Formulation | Oxidative Damage (Cysteic Acid Units) | Lightening (ΔL) | Cycle Time (minutes) |
|---|---|---|---|---|---|
| 1 | 4 | Ulrasound Formulation with EDDS | 103.1 | 24.43 | 10 |
| 2 | 3 | Ultrasound Control Formulation | 176.5 | 20.70 | 10 |
| 3 | | Conventional Formulation with EDDS | 135.1 | 26.72 | 30 |
| 4 | | Conventional Control Formulation | 182.2 | 25.88 | 30 |

Figure 2:
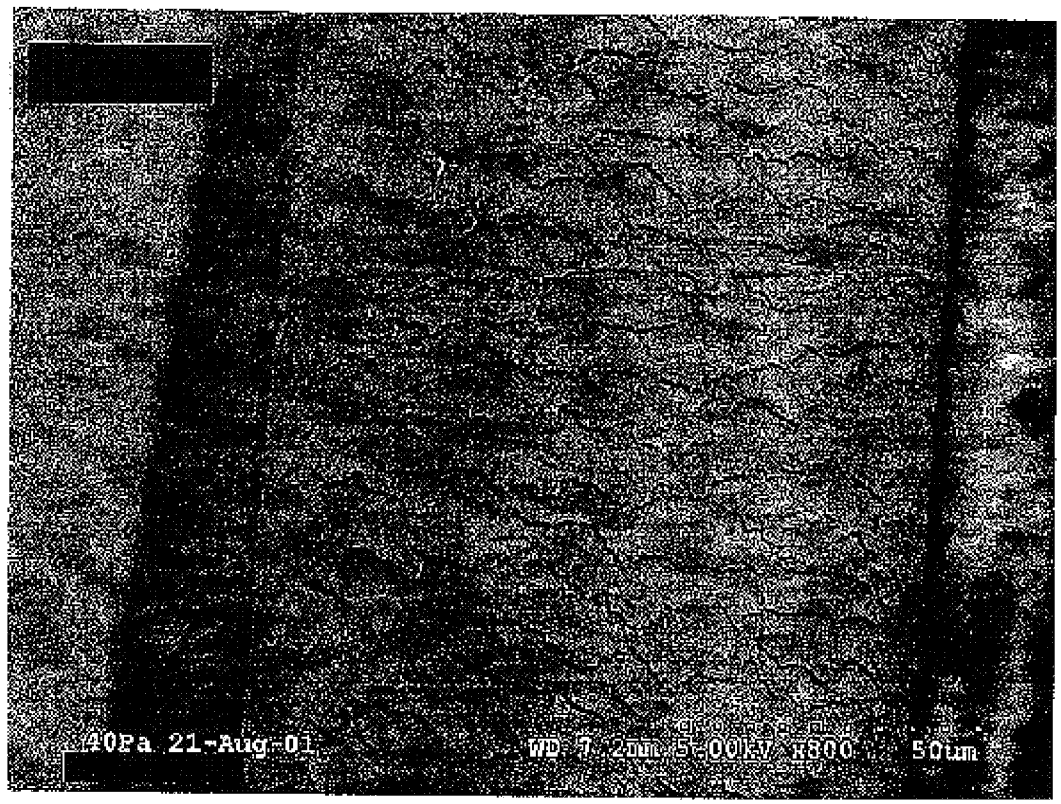
FIG. 2 is a prior art SEM image of untreated keratinous fibers.
Figure 3:
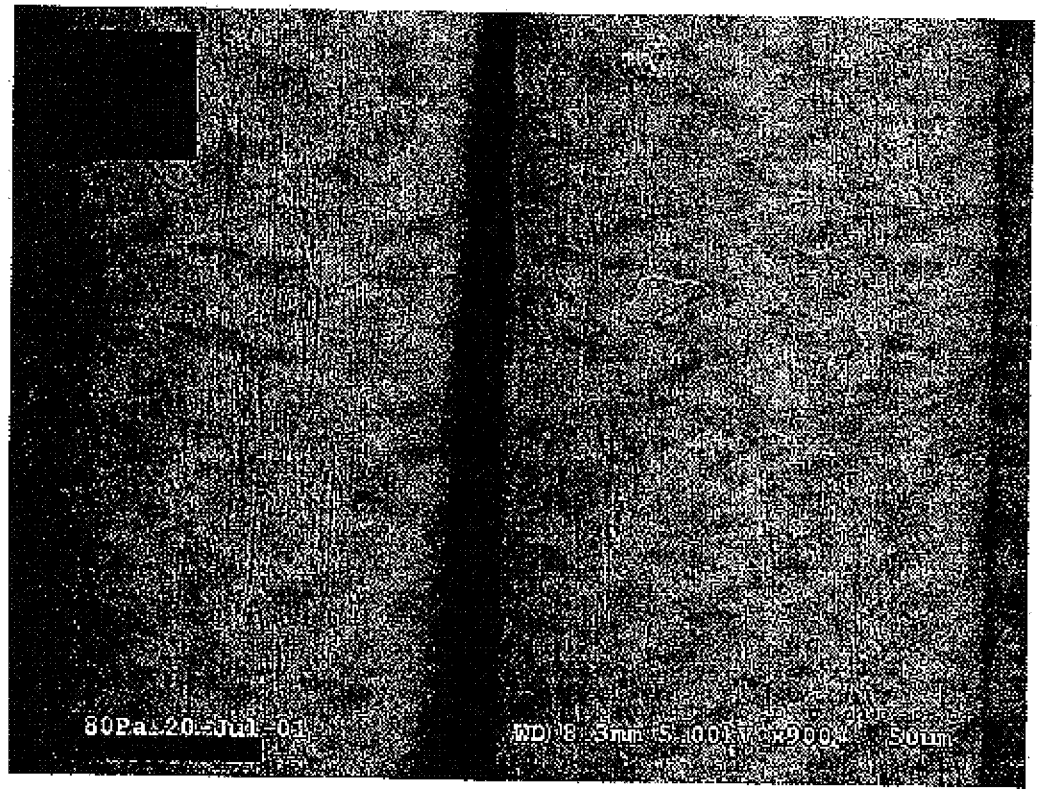
FIG. 3 is a prior art SEM image of ultrasonically treated keratinous fibers without an applied chelating agent; and, FIG. 4 is an SEM image of ultrasonically treated keratinous fibers with a chelating agent applied.
Figure 4:
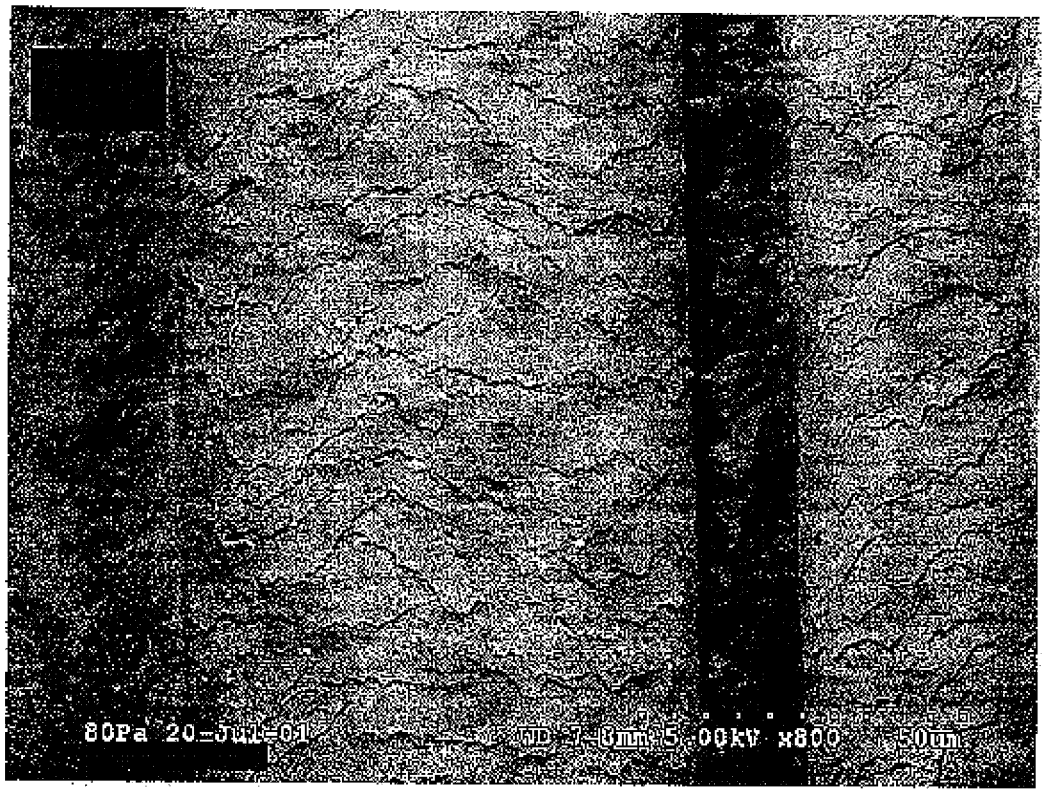

FIG. 2 is a prior art SEM image 20 of normal, untreated keratinous fibers 21. FIG. 3 is a prior art SEM image 30 of a damaged cuticle 31 resulting from not using a chelating agent in accord with the present invention. FIG. 4 is an SEM image 40 of ultrasonically treated keratinous fibers 41 with an applied chelating agent in accordance with the disclosure discussed supra. As FIG. 3 depicts, the total loss of cuticle 31 can be a catastrophic event resulting in negative hair quality aspects.

The foregoing examples and descriptions of the preferred embodiments are not intended to be exhaustive or to limit the invention to the precise forms disclosed, and modifications and variations are possible and contemplated in light of the above teachings. Accordingly, it is intended that such modifications fall within the scope of the invention as defined by the claims appended hereto.

What we claim is:

1. A process for the oxidative treatment of at least one keratinous fiber comprising the steps of:
   (a) placing a chelant proximate to said at least one keratinous fiber;
   (b) placing an ultrasonic treatment device proximate to said keratinous fiber;
   (c) energizing said ultrasonic treatment device to produce a topically efficacious energy; and,
   (d) applying said topically efficacious energy from said ultrasonic treatment device to said keratinous fiber;
   wherein said topically efficacious energy efficaciously deposits said chelant onto said keratinous fiber.

2. The process of claim 1 wherein said step (a) comprises selecting said chelant from the group consisting of diamine-N,N'-dipolyacids, monoamine monoamide-N,N'-dipolyacids, N,N'-bis(2-hydroxybenzyl)ethylenediamine-N,N'-diacetic acids, precursors thereof, salts thereof, and combinations thereof.

3. The process of claim 2 wherein said step (a) comprises selecting said chelant from the group consisting of ethylenediamine-N,N'-disuccinic acid (EDDS), ethylenediamine-N,N'-diglutaric acid (EDDG), 2-hydroxypropylenediamin-N,N'-disuccinic acid (HPDDS), glycinamide-N,N'-disuccinic acid (GADS), ethylenediamine-N-N'-bis(ortho-hydroxyphenyl) acetic acid (EDDHA), precursors thereof, salts thereof, and combinations thereof.

4. The process of claim 1 wherein said step (c) comprises energizing said ultrasonic treatment device at a frequency from about 15 KHz to about 500 KHz.

5. The process of claim 4 wherein said step (c) comprises energizing said ultrasonic treatment device at a frequency from about 20 KHz to about 150 KHz.

6. The process of claim 1 wherein said ultrasonic treatment device comprises a comb device coupled to an ultrasound generator wherein said comb device is responsive to said topically efficacious frequency.

7. The process of claim 6 wherein said ultrasonic treatment device comprises:
   a first material reservoir for supplying a first material; and,
   a second material reservoir for supplying a second material; and,
   wherein said first material reservoir and said second material reservoir are in liquid communication with said comb device.

8. The process of claim 7 wherein at least a portion of at least one of said first or second reservoirs are removeably contained within said fiber treatment device.

9. The process of claim 1 wherein said step (a) further comprises providing said chelant at a concentration ranging from at least about 0.5 percent by weight to at least about 10 percent by weight.

10. The process of claim 9 wherein said chelant is provided at a concentration ranging from at least about 2 percent by weight to at least about 5 percent by weight.

11. The process of claim 1 wherein said oxidative treatment is selected from the group consisting of hair bleaching, hair highlighting, hair dyeing, hair perming, hair straightening, and combinations thereof.

12. The process of claim 1 further comprising the step of:
   (e) rinsing a portion of said chelant from said at least one fiber.

13. The process of claim 1 wherein said at least one keratinous fiber has a relative oxidative damage number of less than about 150 cysteic acid units after five treatment cycles.

14. A kit to provide for the oxidative treatment of keratinous fibers, said kit comprising:
   (a) at least one chelant selected from the group consisting of diamine-N,N'-dipolyacids, monoamine monoamide-N,N'-dipolyacids, N,N'-bis(2-hydroxybenzyl)ethylenediamine-N,N'-diacetic acids, precursors thereof, salts thereof, and combinations thereof; and
   (b) at least one active agent;
   wherein said at least one chelant and said at least on active agent are combined in a container.

15. The kit of claim 14 further comprising:
   (c) an ultrasonic fiber treatment device wherein said device is adapted to produce a frequency topically efficacious for use with said at least one chelant and/or said at least one active agent.

16. The kit of claim 15 wherein said at least one chelant and/or said at least one active agent is provided in at least one reservoir, said at least one reservoir being contained within said ultrasonic fiber treatment device.

17. The kit of claim 15 wherein at least one of said at least one chelant and/or at least one active agent is provided in at least one reservoir, said at least one reservoir being at least partially insertable into said ultrasonic fiber treatment device.

18. The kit of claim 15 wherein a user may selectively dispense said at least one chelant and/or at least one active agent from said fiber treatment device.

19. The kit of claim 14 wherein the ratio of said at least one active agent to said at least one chelant is from about 20:1 to about 1:20 weight/weight.

20. A process for the oxidative treatment of keratinous fibers comprising the steps of:

providing an ultrasonic treatment device comprising a comb device, a first material reservoir for supplying a first material, and a second material reservoir for supplying a second material, wherein said first material reservoir and said second material reservoir are in liquid communication with said comb device;

dispensing at least one of said first material or said second material from said ultrasonic treatment device onto said keratinous fibers;

energizing said ultrasonic treatment device to produce a topically efficacious energy; and, applying said topically efficacious energy from said ultrasonic treatment device to said keratinous fibers.

* * * * *